Figure 1:
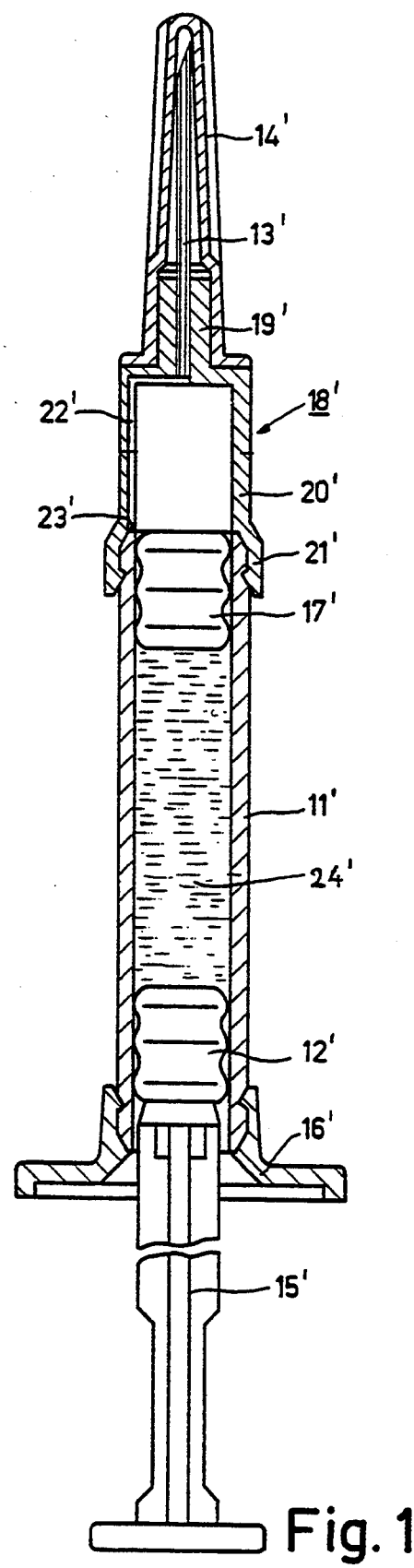

United States Patent [19]

van den Heuvel

[11] Patent Number: 5,383,864
[45] Date of Patent: Jan. 24, 1995

[54] PRE-FILLED INJECTION DEVICE COMPRISING A BARREL WHEREIN A LIQUID DIAZEPAM FORMULATION IS ACCOMMODATED

[75] Inventor: Johan G. van den Heuvel, Amsterdam, Netherlands

[73] Assignee: Duphar International Research B.V.

[21] Appl. No.: 990,929

[22] Filed: Dec. 14, 1992

Related U.S. Application Data

[63] Continuation of Ser. No. 497,669, Mar. 23, 1990, abandoned.

[30] Foreign Application Priority Data

Mar. 28, 1989 [NL] Netherlands ............... 8900747

[51] Int. Cl.⁶ .................................... A61M 5/315
[52] U.S. Cl. .................. 604/218; 604/232; 604/202
[58] Field of Search .............. 604/192, 194–196, 604/201–202, 218, 232

[56] References Cited

U.S. PATENT DOCUMENTS

| | | | |
|---|---|---|---|
| 4,235,235 | 11/1980 | Bekkering | 604/238 |
| 4,291,695 | 9/1981 | Bekkering et al. | |
| 4,381,779 | 5/1983 | Marguiles | 604/202 |
| 4,447,231 | 5/1984 | Bekkering | 604/226 |
| 4,529,403 | 7/1985 | Kamstra | 604/191 |
| 4,565,543 | 1/1986 | Bekkering et al. | 604/244 |
| 4,822,340 | 4/1989 | Kamstra | |
| 4,893,636 | 1/1990 | Cook et al. | 604/205 |
| 4,983,586 | 1/1991 | Bodor | 514/58 |

FOREIGN PATENT DOCUMENTS

3103897 9/1982 Germany.

OTHER PUBLICATIONS

Goodman & Gilman's *The Pharmacological Basis of Therapeutics*, pp. 352, 437 and 466 (1985).

*Primary Examiner*—C. Fred Rosenbaum
*Assistant Examiner*—Chalin Smith
*Attorney, Agent, or Firm*—Stevens, Davis, Miller & Mosher

[57] ABSTRACT

The invention relates to a pre-filled injection device, comprising (i) a barrel which is open at each end in which, before using the device, a liquid diazepam formulation is accommodated in a sealed manner and which comprises at least one rubber sealing member to seal the said formulation, and (ii) an injection needle or a needle connection at the front end of the barrel, said sealing member being manufactured at least substantially from bromobutyl rubber.

5 Claims, 2 Drawing Sheets

PRE-FILLED INJECTION DEVICE COMPRISING A BARREL WHEREIN A LIQUID DIAZEPAM FORMULATION IS ACCOMMODATED

This application is a Continuation of application Ser. No. 07/497,669, filed Mar. 23, 1990, now abandoned.

The invention relates to a pre-filled injection device, comprising (i) a barrel which is open at each end and in which, before using the device, a liquid diazepam formulation is accommodated in a sealed manner and which comprises at least one rubber sealing member to seal the said formulation, and (ii) an injection needle or a needle connection means at the front end of the barrel.

As is well-known, diazepam has good pharmacotherapeutic properties and is hence generally used as a sedative, as a hypnotic and as a muscle relaxant. Useful formulations for the parenteral administration of diazepam have meanwhile also become available. These liquid formulations comprise, in addition to diazepam and water, auxiliary substances in the form of organic solvents and/or formulation agents. As a result of this a solution or emulsion of diazepam which is suitable for parenteral administration can be obtained by a correct choice and dosing of the auxiliary substances.

Such liquid diazepam formulations are often stored for considerable periods of time. As a result of this, suitable reservoirs are required in which the liquid can be accommodated in a sealed manner. Such reservoirs which usually are manufactured from glass or from a suitable synthetic material which is compatible with the diazepam formulation, are preferably sealingly closed by means of rubber sealing members.

Reservoirs which should permit the long-term storage of injection liquids are found in particular in pre-filled injection devices. There is an increasing demand for such injection devices which are supplied to the user while already filled with injection liquid. These so-called pre-filled injection devices should often be stored for long periods of time before being used and must hence be able to stand up against the conditions in which the devices are stored. This means that the injection devices should be able to still function properly after a storage term guaranteed by the supplier and that the contents of the injection devices, i.e., the injection liquid, may not have suffered any detrimental effects from the storage.

It will hence be obvious that high requirements have to be imposed on such injection devices for the prolonged storage of injection liquids, both as regards to the maintenance of mechanical properties of the injection device. and as regards the preservation of the injection liquid during the storage period. Much attention has been paid to the choice and optional pre-treatment of the rubber sealing members for the barrels of such injection devices in which the injection liquids are sealingly stored before use of the devices. Of course, the type of rubber must be completely inert with respect to the medicament to be injected, also during the often long storage period, but must moreover satisfy high requirements as regards the impermeability to gases, in particular oxygen, and be sufficiently resistant to the external influences to which the injection device is exposed during storage, for example, heat, air oxygen and light, in particular UV-light. In addition to the said physico-chemical requirements which the selected type of rubber must satisfy, the rubber sealing members should have certain mechano-dynamical properties. This applies in particular to the piston and to the stopper or stoppers optionally movable in the barrel, which on the one hand must well seal the injection liquid in the barrel before use of the injection device, but on the other hand must easily be movable in the barrel during use of the device. Of course, the shape of the piston and of the stopper(s) plays an important part in said easy movability in the barrel, as well as the desired pre-treatment, for example, with silicon oil. High demands should equally be made upon the mechanical properties of sealing members having a central diaphragm which bursts under pressure and then permits the injection liquid to reach the needle. It will be obvious that said diaphragm should remain its sealing function prior to use of the syringe, but should burst open at the proper instant to allow passage of the injection liquid.

Butyl rubbers including bromobutyl rubber and chlorobutyl rubber, can be used for the manufacture of pistons for injection devices; this is disclosed, e.g., in U.S. Pat. No. 4,381,779. Chlorobutyl rubber has been found to be an excellent material for the manufacture of sealing members for reservoirs, in particular for barrels for injection devices. Sealing members manufactured from chlorobutyl rubber satisfy the above-mentioned requirements excellently, while in general the medicaments present in the injection liquid do not experience any detrimental influence from prolonged contact with this type of rubber. Liquid diazepam formulations, i.e., diazepam formulations for parenteral administration, however, constitute an exception. As a matter of fact it has been found that the shelf-life of the said formulations, after prolonged contact with chlorobutyl rubber sealing members, leaves to be desired. This is a serious disadvantage because as a result of this not only the concentration of diazepam decreases during the storage period, as a result of which a smaller quantity of the therapeutic than is desired is injected, but also undesired by-products may be formed which may arrive in the patient's body.

It is the object of the present invention to provide a pre-filled injection device as defined in the opening paragraph, comprising a barrel, wherein a liquid diazepam formulation can be stored in prolonged contact with at least one rubber sealing member without unacceptable deterioration in quality of the said formulation taking place.

This object can be achieved by means of an injection device, comprising a barrel in which a liquid diazepam formulation, sealingly closed by at least one sealing member, is accomodated, which device is characterised according to the present invention in that said sealing member is manufactured at least substantially from bromobutyl rubber.

Bromobutyl rubber consists of a bromine-containing copolymer of isobutene and isopropene as a basic elastomer to which fillers, auxiliary substances, pigments and the like are added in certain concentrations to obtain the desired properties. After vulcanization a rubber quality is obtained which—like the chlorobutyl rubber described hereinbefore—has the properties required for sealing members, in particular sealing members for the barrels of injection devices. As will become apparent from the examples, however, bromobutyl rubber—in contrast with chlorobutyl rubber—causes no unacceptable deterioration in quality of a liquid diazepam formulation in prolonged contact herewith.

Many examples are to be found in literature of pre-filled injectors in which the injection liquid is sealingly enclosed between a piston and a stopper with pierceable central portion said stopper being rigidly connected to the front end of the barrel. When using such an injector, said central portion is pierced so that the injection liquid can reach the injection needle and can be injected. In a favourable modified embodiment the stopper rigidly connected to the barrel comprises centrally a diaphragm which bursts under pressure and thus permits the injection liquid to reach the needle; an example hereof is to be found in Netherlands Patent Application No. 7603511 in the name of the Applicants. More recently, one has proceeded to enclosing the injection liquid between a piston and a stopper which is movable in the barrel; see, for example, Netherlands Patent Application No. 7714308, also in the name of Applicants. When such an injector is used, both the piston and the stopper and the intermediately situated injection liquid are removed forward in the barrel, in which the stopper is moved out of its sealing position and the injection liquid can reach the injection needle past the stopper. By using several stoppers, such injection device can be made suitable for accommodating therein several injection liquids which may not be in contact with each other during the storage period.

In such pre-filled injection devices, the liquid diazepam formulation can be stored in the barrel while enclosed between two rubber sealing members. According to the invention, these injection devices comprise two sealing members of bromobutyl rubber with which the diazepam formulation can be in prolonged contact without deterioration of the quality of said formulation.

Automatic injection devices—or autoinjectors—actually constitute a special category within the pre-filled injection devices. In fact, automatic injection devices are also pre-filled with injection liquid; they are, however, intended for being used by unqualified persons. For that purpose they are constructed so that the injection liquid can be administered automatically by a person not trained in giving injections. Consequently, automatic injection devices are designed first of all for use by persons who at a given instant, which is not known beforehand, have to administer an injection into their own body. These persons include, for example, soldiers after they have been exposed to an enemy warfare gas, for example, a nerve gas. However, many of the medicaments used in automatic injection devices show undesired side effects or are insufficiently or incompletely active in therapeutic dosages. For example, atropine or obidoxim is generally used in an attack with nerve gas in order to neutralise the toxic effects of organophosphate poisons, the active constituents of most nerve gases. However, these organophosphate poisons also cause paralyses or spasm conditions of the muscles which are insufficiently controlled by the above-mentioned medicaments. Therefore, the activity of the said medicaments is often made up with benzodiazepines, for example diazepam, which is known to have a muscle-relaxing activity. Diazepam in a liquid formulation, suitable for parenteral administration, is preferably accommodated in the injection device while separated from the other medicaments in view of the mutual compatibility. Suitable multi-compartment automatic injectors in which several injection liquids can be accommodated while separated from each other are disclosed, for example, in European Patent Applications 72057 and 219899, both in the name of the Applicants. In addition to the therapeutic activity mentioned herebefore, diazepam also has a sedative effect, as a result of which the fighting value of the soldiers at the front is restored. For this latter purpose the soldier in the field is preferably provided with a separate automatic injection device which is filled with a liquid diazepam formulation. Such an injector is especially intended for appeasing a buddy in the battle field who has panicked as a result of war acts or injuries: "buddy aid".

It will be obvious from the above that still considerably higher requirements regarding the reliability have to be imposed upon automatic injectors than upon pre-filled non-automatic injection devices. Such injectors are usually stored for many years at a time and, moreover, will be kept by the potential users for long periods of time under varying conditions; not only the proper operation of the injection devices must be sufficiently ensured, but the contents of the autoinjectors, i.e., the injection liquid or injection liquids, must, of course, remain sufficiently intact to ensure the intended therapeutic activity.

The present invention therefore also relates more in particular to such an automatic injection device for the prolonged storage of a liquid diazepam formulation, comprising, in addition to a power source, a barrel which is open at each end, to the front end of which an injection needle is attached and in which a diazepam formulation is accommodated between rubber sealing members, the sealing members being manufactured at least substantially from bromobutyl rubber. It has been found that the stringent stability requirements mentioned hereinbefore can be satisfied when bromobutyl rubber sealing members are used in an automatic injection device.

As stated hereinbefore, bromobutyl rubber is a match for chlorobutyl rubber, known for this purpose, as regards the mechano-dynamic properties. This means that bromobutyl rubber is excellently suitable for the manufacture of piston and stoppers which, when using automatic injectors, must move in the barrel thereof so as to permit the injection liquids to be expelled. Automatic injectors, for example, as disclosed in the European Patent Applications 77057 and 219899 mentioned hereinbefore, in which the diazepam formulation is accommodated between two stoppers which are movable in the barrel or between a piston which is movable in the barrel and a stopper which is also movable herein, may hence advantageously comprise stoppers or a piston and a stopper which are manufactured from bromobutyl rubber.

The invention will now be described in greater detail with reference to the ensuing specific example.

EXAMPLE

Storage Stability Test of Liquid Diazepam Formulations Between Rubber Stoppers

A liquid diazepam formulation is prepared by making up 5 mg of diazepam, 0.4 ml of propylene glycol, 0.1 ml (100%) of ethanol, 0.015 ml of benzyl alcohol, 48 mg of sodium benzoate and 2 mg of benzoic acid with water to a volume of 1 ml. The pH of the resulting solution is 6.7. Rubber stoppers and a glass barrel which is open at each end and has a diameter of 11.4 mm are pre-treated in the conventional manner by washing, siliconising and sterilising. The barrel is then dispensed with the above diazepam formulation and sealed at each end by means of the rubber stoppers. For the experiments three types of rubber are compared with each other, namely chlorobutyl rubber (Cl-bu), and two qualities of bromobutyl rubber: Br-bu 1 and Br-bu 2. The barrels are stored at a given temperature for a given period of time, after which the diazepam concentration is determined by means of HPLC. The decrease of the diazepam content (in percent) is recorded in the Table A below. The analyses have been carried out in triplicate: the recorded data are average results.

TABLE A

| | | Decrease diazepam content after ... (t) at ... (T) | | |
|---|---|---|---|---|
| | | % decrease diazepam using ... rubber | | |
| T (°C.) | t (weeks) | Cl-bu | Br-bu 1 | Br-bu 2 |
| 31 | 13 | 5.9 | 2.7 | 2.9 |
| 41 | 6 | 6.7 | 2.7 | 2.9 |
| 41 | 13 | 11.4 | 3.3 | 3.7 |
| 61 | 3 | 19.1 | 5.1 | 5.3 |
| 61 | 6 | 25.3 | 6.5 | 7.0 |
| 61 | 13 | 42.2 | 12.1 | 14.9 |

The experiments have been repeated with a liquid diazepam formulation comprising 6 mg of diazepam instead of 5 mg diazepam. The results are recorded in Table B.

TABLE B

| | | Decrease diazepam content after ... (t) at ... (T) | | |
|---|---|---|---|---|
| | | % decrease diazepam using ... rubber | | |
| T(°C.) | t (weeks) | Cl-bu | Br-bu 1 | Br-bu 2 |
| 31 | 13 | 6.8 | 2.4 | 3.0 |
| 41 | 6 | 7.0 | 2.7 | 3.4 |
| 41 | 13 | 11.6 | 3.4 | 4.1 |
| 61 | 3 | 20.3 | 4.7 | 5.8 |
| 61 | 6 | 27.6 | 6.8 | 8.0 |
| 61 | 31 | 43.5 | 12.7 | 15.9 |

It will be obvious from the above results that the chlorobutyl stoppers cause a considerably larger decrease of the diazepam content than the stoppers manufactured from the two qualities of bromobutyl rubber. The diazepam concentration, namely 6 with respect to 5 mg/ml, has no essential influence on the said decrease.

Figure 2:
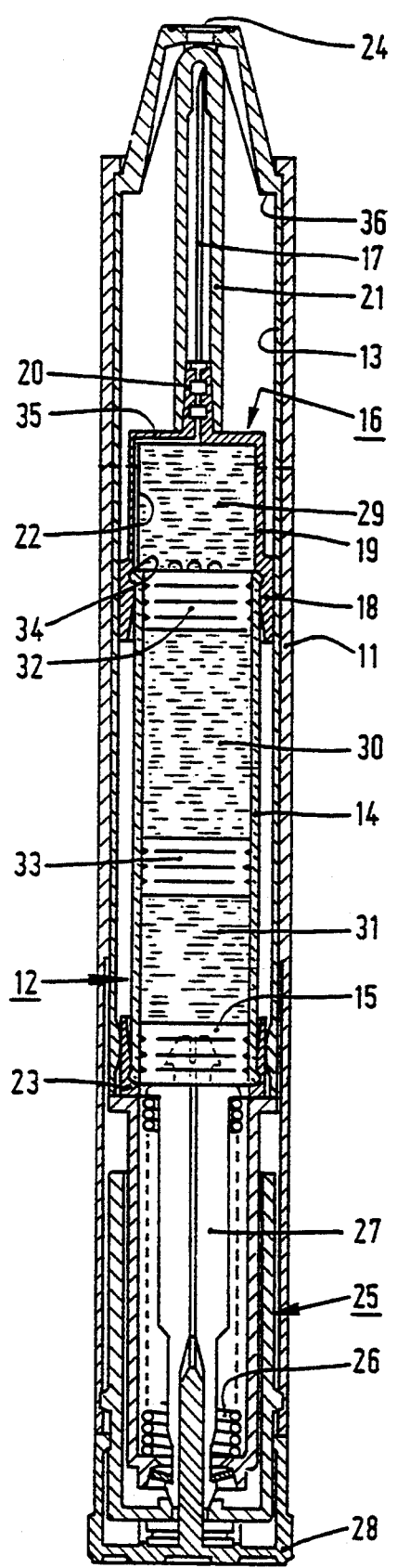
Figure 3:
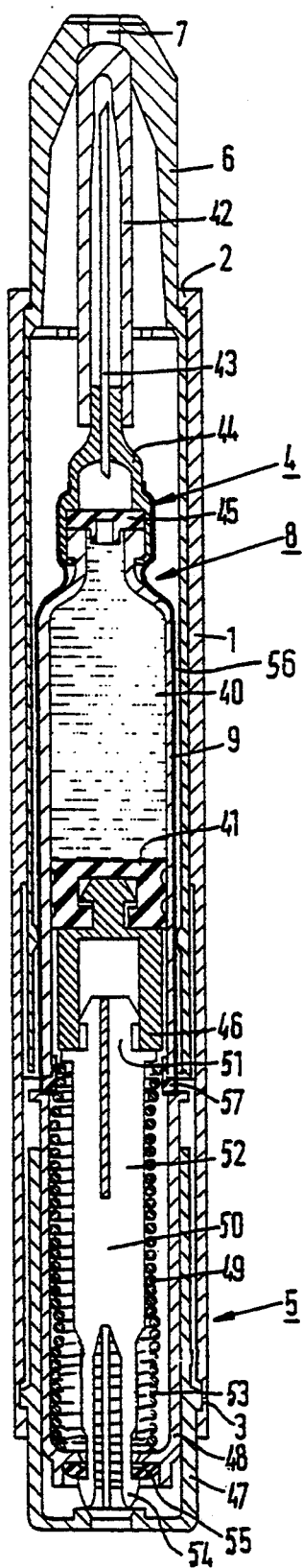

Examples of pre-filled injection devices are presented in the accompanying drawings, wherein FIG. 1 is a longitudinal sectional view of a manually operated pre-filled injection device according to the present invention, shown in the condition in which it can be transported and stored; and FIGS. 2 and 3 are longitudinal sectional views of automatic injection devices or autoinjectors according to the present invention, equally shown in their storage conditions.

The injection device shown in FIG. 1 comprises a barrel 11', in which a plunger 12' is provided on one end while the other end comprises an injection needle 13' covered by a needle guard 14', keeping the needle in a sterile condition during storage. The plunger 12' can be moved by a plunger rod 15' and the barrel has a finger grip 16'. A stopper 17' sealing the barrel is situated in the end of the barrel remote from the plunger. Both the plunger and the stopper are manufactured from bromobutyl rubber and enclose a liquid diazepam formulation 24'. Further the injection needle 13' is secured to the barrel by means of a needle holder 18', comprising a neck 19' for sealingly gripping the needle, a shaft 20' and a collar 21'. One or more slots 22' are recessed in the inner wall of the shaft and the rear face of the neck, allowing the injection liquid 24' to pass the stopper when during use of the device said stopper has been moved in a forward position until portion 23' of said slot or slots has become uncovered. The FIG. 1 embodiment as well as its use are described in greater detail in U.S. Pat. No. 4,235,235.

The automatic injection device shown in FIG. 2 comprises a cylindrical outer sleeve 11, in which a cartridge assembly 12 is slidably accommodated. Said cartridge assembly comprises a cartridge holder sleeve or inner sleeve 13, fitting in the outer sleeve, a cylindrical glass barrel 14 containing injection liquids, a piston 15 at one end and a needle holder 16 with injection needle 17 at the other end of the barrel. The needle holder comprises a collar 18, a shaft 19 and a neck 20, wherein said needle 17, covered by a flexible needle guard 21, is connected. One or more slots 22 are recessed in the inner wall of the shaft and the rear wall of the neck, allowing the injection liquids to reach the needle upon actuation of the device. At its backmost portion the barrel is provided with a sliding sleeve 23. The closed end of the needle guard 21 bears against the end of the cartridge holder sleeve 13 having bore 24. The outer sleeve has a length such that the cartridge assembly 12 is accommodated in one end thereof and a discharge mechanism 25 in the other. This discharge mechanism is the same as in the FIG. 3 embodiment described hereinafter and comprises a coil spring 26, locking means 27 and a safety device 28. Internally the barrel is divided into three separated liquid compartments 29, 30 and 31 by means of two cylindrical stoppers 32 and 33 which, like the piston, have a slightly larger diameter than the inside diameter of the barrel. These stoppers, as well as the piston, are manufactured from bromobutyl rubber. The injection liquid in compartment 31 or, alternatively, the injection liquid in compartment 30 consists of a liquid diazepam formulation. The use of the autoinjector shown in FIG. 2 is described in greater detail in U.S. Pat. No. 4,529,403, in particular in the paragraphs relating to the embodiment shown in FIGS. 1 and 2 thereof.

Finally the autoinjector presented in FIG. 3 comprises an outer sleeve 1 having an inward edge 2 and a circumferential groove 3, in which, a cartridge assembly 4 and a discharge mechanism 5 are accommodated. The cartridge assembly comprises a cartridge holder 6, which fits in the outer sleeve and has on its front end a circular aperture 7, and a cartridge 8 which is movable in the cartridge holder. The cartridge comprises a barrel 9 with injection liquid 40, a piston 41 at one end and a needle 43 having a flexible needle guard 42 at the other end, said needle being connected to the barrel by means of a needle holder 44. A membrane 45 is provided between the neck of the barrel and the needle holder, which, during storage of the injector, keeps the injection liquid separated from the needle but, during use of the injector, bursts open so that the injection liquid can reach the needle. Further a spacer 46 is provided to reduce the volume for injection liquid in the barrel. The discharge mechanism 5 comprises an outer gun sleeve 47 locked (at 3) in the outer sleeve 1, an inner gun sleeve 48 and a coil spring 49, fitting around a plunger 50. Said plunger consists of a plunger head 51, inserted into the spacer, a central portion 52 and an end portion 53 consisting of four resilient prongs or detent arms the conical ends 54 of which bear on a metal ring 55 around an aperture in the rear face of the inner gun sleeve. A sheath 56 of PVC shrinkable sheet is shrunk around the barrel, including its neck portion. An annular member 57 is provided on the rear edge of the barrel. For more details as to the function of the various parts of the FIG. 3 injector reference is made to U.S. Pat. No.

4,565,543. Both the piston 41 and the membrane 45 are manufactured from bromobutyl rubber and enclose a liquid diazepam formulation as the injection liquid 40.

I claim:

1. A pre-filled injection device, comprising (i) a barrel which is open at each end in which, before using the device, a liquid diazepam formulation is sealingly accommodated and which comprises at least one rubber sealing member to seal said formulation, and (ii) a needle connection means for connecting an injection needle at the front end of the barrel, wherein said sealing member is manufactured from bromobutyl rubber.

2. An injection device as claimed in claim 1, in which the liquid diazepam formulation, before using the device, is sealingly accommodated between two rubber members in the barrel, wherein the sealing members are manufactured from bromobutyl rubber.

3. A pre-filled injection device for the automatic injection of injection liquid under the influence of a power source, comprising, in addition to the power source, a barrel, which is open at each end, to the front end of which an injection needle is attached and in which a liquid diazepam formulation is accommodated between two rubber sealing members, wherein the sealing members are manufactured from bromobutyl rubber.

4. An automatic injection device as claimed in claim 3, in which the diazepam formulation is accommodated between two stoppers which are movable in the barrel wherein both stoppers are manufactured from bromobutyl rubber.

5. An automatic injection device as claimed in claim 3, in which the diazepam formulation is accommodated between a piston and a stopper, each of which is movable in the barrel, wherein the piston and the stopper are manufactured from bromobutyl rubber.

* * * * *